(12) United States Patent
Bajusz et al.

(10) Patent No.: US 6,235,707 B1
(45) Date of Patent: May 22, 2001

(54) ANTICOAGULANT PEPTIDYL-ARGININE ALDEHYDE DERIVATIVES

(75) Inventors: Sándor Bajusz; Attila Juhász; Éva Barabás; András Fehér; Gabriella Szabó; Erzsébet Széll née Hasenöhrl; Irén Véghelyi née Fauszt; Emilia Lavich née Oszko; Éva Kaszás; József Langó; Imre Moravcsik; Ágnes Szeker née Peszeky; Zsuzsanna Taschler née Pásztor; Gábor Tóth; Zsuzsanna Mohai née Nagy; Anna Mária Szalkay née Hollósi, all of Budapest; Klára Makk née Ocskay, Kismaros, all of (HU)

(73) Assignee: Gyogyszerkutato Intezet Kft., Budapest (HU)

( * ) Notice: Subject to any disclaimer, the term of this patent is extended or adjusted under 35 U.S.C. 154(b) by 0 days.

(21) Appl. No.: 09/194,124

(22) PCT Filed: Jun. 5, 1997

(86) PCT No.: PCT/HU97/00028

§ 371 Date: Nov. 23, 1998

§ 102(e) Date: Nov. 23, 1998

(87) PCT Pub. No.: WO97/46576

PCT Pub. Date: Dec. 11, 1997

(30) Foreign Application Priority Data

Jun. 5, 1996 (HU) .................................................. 9601526

(51) Int. Cl.$^7$ .............................. C07K 5/08; A61K 38/06
(52) U.S. Cl. .................................. 514/2; 514/8; 514/19; 514/22; 530/331
(58) Field of Search .............................. 514/2, 19, 8, 22; 530/331

*Primary Examiner*—Bennett Celsa
(74) *Attorney, Agent, or Firm*—Keil & Weinkauf

(57) ABSTRACT

The invention relates to new peptidyl-arginine aldehyde compounds of formula (I)

Q-D-Xaa-Pro-Arg-H               (I)

wherein
Q represents an acyl group of formula Q'—OCO, wherein Q' represents an alkyl-group with 1–3 carbon atoms,
D-Xaa represents a 3-cyclobutyl-D-alanyl- or 3-cyclopentyl-D-alanyl group,
Pro represents an L-prolyl group, and
Arg represents an L-arginyl group,
and acid-addition salts thereof, and pharmaceutical compositions comprising them, which are suitable for the prevention and cure of thrombosis and accelerated blood clotting.

7 Claims, No Drawings

ANTICOAGULANT PEPTIDYL-ARGININE ALDEHYDE DERIVATIVES

This application is a national stage application under 35 U.S.C. §371 of International Application PCT/HU 97/00, 028, filed Jun. 5, 1997.

This invention relates to new peptidyl-arginine aldehyde derivatives of general formula (I), Q-D-Xaa-Pro-Arg-H       (I)

wherein

Q represents an acyl group of formula Q'—O—CO—, wherein Q' represents an alkyl group with 1–3 carbon atoms, D-Xaa represents a 3-cyclobutyl-D-alanyl or 3-cyclopentyl-D-alanyl group, Pro stands for an L-prolyl residue, and Arg stands for an L-arginyl residue, and their acid-addition salts formed with an organic or inorganic acids and pharmaceutical compositions containing the same.

The new compounds of general formula (I) have valuable therapeutic, particularly anticoagulant, anti-platelet and anti-thrombotic properties.

Particularly preferred representatives of the compounds of general formula (I) of the invention are the following derivatives:

ethoxycarbonyl-3-cyclobutyl-D-alanyl-L-prolyl-L-arginine aldehyde, methoxycarbonyl-3-cyclobutyl-D-alanyl-L-prolyl-L-arginine aldehyde, ethoxycarbonyl-3-cyclopentyl-D-alanyl-L-prolyl-L-arginine aldehyde, methoxycarbonyl-3-cyclopentyl-D-alanyl-L-prolyl-L-arginine aldehyde, and their acid-addition salts with organic and inorganic acids, preferably the hemisulfate salts.

Definitions

The abbreviations of the amino acids, their substituents and peptides built up therefrom are in accordance with the prior art, e.g. Biochem. J. 126, 773 (1972); Biochemistry 14, 449 (1975).

Amino acids:

Arg=L-arginine[(2R)-2-amino-5-guanidino-pentanoic acid],

Asp=L-aspartic acid[(2S)-2-amino-3-carboxypropionic acid], boroArg=L-boroarginine[(1R)-1-amino-4-guanidinobutylboric acid], D-Cba=3-cyclobutyl-D-alanine[(2R)-2-amino-3-cyclobutylpropionic acid], DL-Cbg=DL-cyclobutyl-glycine[(2RS)-2-amino-2-cyclobutylacetic acid], D-Chg=D-2-cyclohexyl-glycine[(2R)-2-amino-cyclohexylacetic acid], D-Cpa=3-cyclopentyl-D-alanine[(2R)-2-amino-3-cyclopentylpropionic acid], Gla=gamma-carboxy-L-glutamic acid[(2S)-2-amino-4,4-dicarboxybutyric acid], Glu=L-glutamic acid[(2S)-2-amino-4-carboxybutyric acid], Glp=L-pyroglutamic acid[(5S)-2-pyrrolidone-5-carboxylic acid], Gly=glycine (2-aminoacetic acid), D-MePhe=N-methyl-3-phenyl-D-alanine[(2R)-2-methylamino-3-phenylpropionic acid], D-MePhg=D-N-methyl-phenylglycine[(2R)-2-amino-2-phenylacetic acid], Nal(1)=3-(naphth-1-yl)-L-alanine[(2S)-2-amino-3-(naphth-1-yl)-propionic acid], D-Phe=3-phenyl-D-alanine[(2R)-2-amino-3-phenylpropionic acid], Pro=L-proline[(2S)-pyrrolidine-2-carboxylic acid].

Substituents:

Ac=acetyl, Boc=t-butoxycarbonyl, Bz=benzoyl, Eoc=ethoxycarbonyl, Et=ethyl, iPoc=isopropoxycarbonyl, Me=methyl, 4MeP=4-methyl-pentanoyl, Moc=methoxycarbonyl, pNA=p-nitrophenylamino, Poc=propoxycarbonyl, Tos=p-toluene-sulfonyl, Z=benzyloxycarbonyl.

TECHNICAL FIELD

The abbreviations of amino acids alone represent the respective L-amino acid. The D-amino acid is marked separately, i.e. 3-phenyl-D-alanine=D-Phe. The hyphen before and after the amino acid abbreviation designates a missing hydrogen atom from the amino group or a missing hydroxy group from the carboxy group, resp. Accordingly, Eoc-D-Cba-Pro-Arg-H represents ethoxycarbonyl-3-cyclobutyl-D-alanyl-L-prolyl-L-arginine aldehyde, while Bz-Ile-Glu-Gly-Arg-pNA represents benzoyl-Lisoleucyl-L-glutamyl-glycyl-L-arginine p-nitroanilide.

BACKGROUND ART

Blood clotting represents part of the protective mechanism in the organism. Induced by a vessel will injury a blood clot is formed to prevent bleeding to death. In addition, vascular diseases, haemostasis and pathological activation of clotting factors may also induce blood clotting. In this case the vessel is obstructed fully or partially, by the intravascular thrombus formed and thrombosis develops. Fibrinolysis represents an other part of the protective mechanism. Here excess blood clots are removed by the enzymes participating in thrombolysis and the dissolution of the thrombus, too.

The blood clotting process is a cascade reaction, a series of catalysed enzyme reactions, where plasma proteins, the so-called clotting factors, are activated consecutively. The factors are marked by Roman numerals, the active form is represented by the letter "a". Trivial names are in use too, thus fibrinogen=factor I (fI), fibrin=factor Ia (fIa), prothrombin=factor II (fII) and thrombin=factor IIa (fIIa). Serine proteases (fXIIa, fVIIa, fXIa, fIXa fXa, fXa and thrombin), some accelerating co-factors (fVa and fVIIIa) and the clottable molecule itself (fibrin) are all formed during the clotting process. fXa and thrombin are the last two factors among the proteases formed. Thrombin, formed upon the action of fXa, initiates the fission of fib-rinogen, resulting in the fibrin clot.

According to the earlier concept of blood clotting mechanism [R. G. MacFarlane, Nature 202, 498 (1964); E. W. Davie and O. D. Ratnoff, Science 145, 1310 (1964)] fX is activated in two ways by an intrinsic and an extrinsic pathway. In the former case the process is initiated by the surface-activated fXII (fXIIa) with the transformation fXI→fXIa which is followed by the reaction fIX→fIXa; fX is activated by fIXa. In the extrinsic pathway the process is initiated by the appearance of the cellular surface receptor, the tissue factor (TF), and the development of the [fVII+TF] or [fVIIa+TF] complex. fX is activated by the [fVIIa+TF] complex.

According to recent findings blood clotting in the living organism is a result of both pathways combined [E. W. Davie et al., Biochemistry 43, 10363 (1991)] where the main steps are the following:

1. In the case of vessel wall injury or disease, TF migrates to the surface and binds a portion of factor VII circulating in the blood. The [fVII+TF]-complex formed is converted by the action of suitable trace amounts of proteases (fXIIa, fXa, fIXa and thrombin) into the active enzyme complex [fVIIa+TF] which activates a small portion of plasma factors IX and X (i.e. small amounts of fIXa and fXa are formed), then it is inactivated by the action of TFPI (Tissue Factor Pathway Inhibitor, earlier name Lipoprotein-Associated Coagulation Inhibitor), the common inhibitor of both fXa and [fVIIa+TF] [T. J. Girard et al., Nature 338, 518–520 (1989)].

2. The fIXa generated together with factor X and cofactor VIIIa produces, in the presence of $CA^{++}$ ions, on a phospholipid surface (PL) the "tenase" complex, [fIXa+fVIIIa+fX+PL+$CA^{++}$], wherein fX is activated to fXa.

3. The fXa generated up to this point, together with prothrombin (fII) and cofactor Va, produces the "prothrombinase complex" [fXa+fVa+fII+PL+$CA^{++}$], which has a structure similar to that of "tenase". Inside this complex prothrombin is converted to thrombin. The fV→fVa and fVIII→fVIIIa conversions can be performed either by fXa or thrombin.

4. The small amount of thrombin generated converts a portion of fXI to the enzyme fXIa and activates some factors VIII and V, to produce further amounts of fVIIIa and fVa, resp. By now fXIa can carry out the conversion of factor IX to the enzyme fIXa. With this step the chain reaction starting with the Xase-complex and terminated with thrombin formation is resumed. With the repetition of the process increasing amounts of thrombin are formed.

5. At a suitable high thrombin concentration the fibrinogen dissolved in the plasma undergoes partial proteolysis, a fibrin-monomer is generated which is first associated to a soluble fibrin polymer, then it is converted to insoluble fibrin polymer. Here also the thrombin is playing a role, as fXIIIa, the factor performing polymerisation, is produced upon its action [L. Lorand and K. Konishi, Arch. Biochem. Biophys. 105, 58 (1964).

The insoluble fibrin polymer is the main component of the blood clot and thrombus, the other being the blood platelet aggregate which is generated primarily upon the action of thrombin, too. The thrombus or blood clot formed entraps the major part of thrombin generated during the process which triggers a new coagulation process when it gets into the solution during the dissolution of the thrombus [A. K. Gash et al., Am. J. Cardiol. 57, 175 (1986); R. Kumar et al., Thromb. Haemost. 72, 713 (1994)].

The above features demonstrate the key role of thrombin in thrombus formation. Consequently all compounds interfering with the function and/or formation of thrombin are of major importance in the therapy of thrombosis At present the most widely and successfully used compounds applied for the prophylaxis and treatment of thrombosis are the heparins and the vitamin K antagonist coumarins (e.g. Syncumar and Warfarin) which are indirect thrombin inhibitors.

Heparin catalyses the reaction between thrombin and its natural inhibitor, antithrombin-III (AT-III). However, this action of heparin is absent if the plasma concentration of AT-III is lower than 75% of the normal level [R. Egbring et al., Thromb. Haemost. 42, 225 (1979)]. It is also of importance that the thrombin bound by the above-mentioned thrombus fails to be inhibited by this indirect mechanism as it is inaccessible to the heparin-AT-III-complex [J. I. Weitz et al., J. Clin. Invest. 86, 385 (1990)]. In addition, side effects such as treatment-related haemorrhages and thromboembolisms developing due to immunopathological processes are not negligible either [J. M. Walenga et al., Clin. Appl. Thrombosis/Haemostasis, 2(Suppl.1), S21–S27 (1996)].

The vitamin K antagonists may be administered orally, too, their effect is developing after 16–24 hours. They inhibit the development of the reactive forms of some Gla-containing clotting factors (I. e. prothrombin). To achieve therapeutic effects partial inhibition (60–70%) is required [M. P. Esnouf and C. V. Prowse, Biochim. Biophys. Acta 490, 471 (1977)] which can be attained by suitable drug dosage. Vitamin K antagonists, however, are difficult to use due to their narrow therapeutic range, strong dependence on diet composition (vitamin K) and variable individual sensitivity.

The first highly potent synthetic compound directly inhibiting thrombin was the tripeptide aldehyde D-Phe-Pro-Arg-H, a reversible inhibitor, exhibiting significant anticoagulant activity both in vitro and in vivo [S. Bajusz et al., in: Peptides: Chemistry, Structure and Biology (R. Walter and J. Meienhofer, Eds.), Ann Arbor Publ., Ann Arbor, Mich., USA, 603–608 (1975); Int. J. Peptide Protein Res. 12, 217 (1978)]. A series of compounds related to D-Phe-Pro-Arg-H have been synthesised. One of the first was Boc-D-Phe-Pro-Arg-H [S. Bajusz et al., Int. J. Peptide Protein Res. 12, 217 (1978)] and the chloromethylketone analogue (D-Phe-Pro-Arg-$CH_2$Cl) which proved to be an irreversible inhibitor [C. Kettner and E. Shaw, Thromb. Res. 14, 969 (1979)]. Further peptides and acylpeptides to be mentioned are the boroarginine analogues (D-Phe- and Boc-D-Phe- as well as Ac-D-Phe-Pro-boroArg) which are potent reversible thrombin inhibitors [C. Kettner et al., J. Biol. Chem. 265, 18289 (1990)] and other analogues of Boc-D-Phe-Pro-Arg-H, including the Boc-D-Chg-Pro-Arg-H analogue [(P. D. Gesellchen and R. T. Shuman, European patent specification No. 0,479,489 A2 (1992)].

In aqueous solutions D-Phe-Pro-Arg-H is prone to undergo spontaneous conversion, but D-MePhe-Pro-Arg-H (GYKI-14766), obtained by methylating the terminal amino group, proved to be of suitable stability while retaining the activity of the parent compound [S. Bajusz et al., U.S. Pat. No. 4,703,036 (1987); J. Med. Chem. 33, 1729 (1990)]. Blood clotting and thrombus formation were significantly inhibited in laboratory animals by the compound [D. Bagdy et al., Thromb. Haemost. 67, 357 and 68, 125 (1992); J. V. Jackson et al., J. Pharm. Exp. Ther. 261, 546 (1992)]; its inhibitory action on the enzymes of fibrinolysis was negligible, co-administered with thrombolytics it significantly promoted the dissolution of the thrombus [C. V. Jackson et al., J. Cardiovascular Pharmacol. 21, 587 (1993)] which could not be attained with the heparin-AT-III complex. Several compounds related to D-MePhe-Pro-Arg-H have been synthesised, e.g. D-MePhg-Pro-Arg-H [R. T. Shuman et al., J. Med. Chem. 36, 314 (1993)].

Anticoagulant activity (i.e. inhibition of the proteolytic reactions in the process) is measured by anticoagulant tests, e.g. in the thrombin time (TT), activated partial thromboplastin time (APTT) and prothrombin time (PT) tests [E. J. W. Bovie et al., Mayo Clinic Laboratory Manual of Haemostasis; W. B. Saunders Co., Philadelphia (1971)]. Plasma, inhibited in spontaneous coagulation, e.g. citrate-plasma, is made to coagulate and the required coagulation time is measured. Upon the action of anticoagulants the coagulation time is prolonged proportionally to the inhibition of the reaction(s) in the process. The anticoagulant effect can be characterised by the substance concentration required to prolong the coagulation time twofold compared to the control ($IC_{50}$). The effect of anticoagulants on individual coagulant proteases is measured by the amidolytic method [R. Lottenberg et al., Methods in Enzymol. 80, 341 (1981); G. Cleason, Blood Coagulation and Fibrinolysis 5, 411 (1994)]. The isolated active factor (e.g. thrombin, fXa) and its chromogen or fluorogen peptide-amide substrate are reacted in the presence or absence of the inhibitor, resp. The enzyme inhibiting action is characterised by the inhibitory constant ($IC_{50}$) measured during amidolysis.

In the TT test coagulation is initiated by the thrombin added to the citrate plasma. In the system 22 pmol/ml of thrombin is functioning and its inhibition can be measured on the fibrinogen (one of the natural substrates of thrombin) in the presence of plasma components. In the APTT and PT tests the full coagulation process takes place. Depending on the activator fX is activated either by the extrinsic or the intrinsic pathway. The generated fXa activates prothrombin to thrombin which, in turn, triggers plasma coagulation. The coagulation time is prolonged if the enzymes or one of them is inhibited by the inhibitor. In the APTT and PT tests at most 40 pmol/ml Xa can be generated (this is the full amount of factor X present in both systems) while 150 pmol/ml (APTT) and 350 pmol/ml (PT) of thrombin are generated [B. Kaiser et al., Thromb. Res. 65, 157 (1992)].

In the case of D-MePhe-Pro-Arg-H (C1) the concentration prolonging clotting time twofold in the TT, APTT and PT tests amounted to 87, 622 and 2915 nM, resp. These values and the amount of thrombin (22, 150 and 350 pmol/ml) functioning in the tests increased similarly, suggesting that C1 behaves in each thrombin inhibitor in both the APTT and the PT tests and has only slight or no influence on the operation of fXa. In good agreement with these results the amidolytic effect of thrombin on Tos-Gly-Pro-Arg-pNA substrate is inhibited by C1 with an $IC_{50}$=2 nM value, while the amidolytic effect of fXa on the corresponding Bz-Ile-Glu-Gly-Arg-pNA substrate was only slightly affected with an $IC_{50}$=9, 1 mM value (Bajusz et al. Unpublished results).

It is an inherent characteristic of the blood clotting mechanism that the process is inhibited not only by direct thrombin inhibitors but also by factors hindering thrombin formation, e.g. fXa inhibitors. The 60-member polypeptide isolated from tick, TAP (Tick Anticoagulant Peptide) [L. Waksman et al., Science 248, 593 (1990); A. B. Kelly et al., Circulation 86, 1411 (1992)] and DX-9065a (C2), a synthetic non-peptide, (+)-(2S)-2-[4[[(3S)-1-acetimidoyl-3-pyrrolidinyl]oxy]phenyl]-3-[7[amidino-2-naphthyl]-propionic acid hydrochloride pentahydrate [T. Hara et al., Thromb. Haemost. 71, 314 (1994); T. Yokoyama et al., Circulation 92, 485 (1995)] are strong inhibitors of blood clotting and thrombus formation. Both the amidolytic effect of fXa and plasma clotting are strongly inhibited in the PT and APTT tests by these compounds, i.e. both the free and the complex-bound Xa factors are equally well inhibited while according to their nature as specific fXa inhibitors thrombin is not inhibited at all, i.e. they fail to exert any activity in the TT test. 4-MeP-Asp-Pro-Arg-H (C3) (international patent application No. 93/15756) and Boc-D-Phe-Nal(1)-Arg-H (C4) (international patent application No. 95/13693) are synthetic peptide inhibitors of fXa.

According to the literature C3 and C4 inhibit the amidolytic activity of fXa on the Z-D-Arg-Gly-Arg-pNA substrate at $IC_{50}$=57 and 30 nM, resp. No data are available on their anticoagulant potency. In our own tests C3 and C4 exhibited also significant inhibition on the Bz-Ile-Glu-Gly-Arg-pNA substrate while their anticoagulant activity proved to be negligible in the plasma clotting tests. The published (C2) and measured (C3–C4) activities of synthetic fXa inhibitors compared to the antithrombin compound C1 are presented in Table 1.

The data of Table 1 demonstrate that in the case of C1 the anticoagulant effect is due to the inhibition of thrombin while in the case of C2 to the inhibition of fXa. The significant fXa inhibitory effect of C3 and C4 is not accompanied by any significant anticoagulant effect. Most probably the fXa active centre in the prothrombinase complex is inaccessible to C3 and C4, these peptides can inhibit only free fXa in solution.

TABLE 1 fXa inhibiting (A) and anticoagulant (B) effect of known synthetic inhibitors

| Inhibitor | A: $IC_{50}$, nM[b] | B: $IC_{50}$, $\mu M^a$ | | |
|---|---|---|---|---|
| | | PT | APTT | TT |
| C1 | 9133 | 2.91 | 0.62 | 0.09 |
| C2 | 70 | 0.52 | 0.97 | $NA^c$ |
| C3 | 64 | 19.32 | 4.59 | 0.87 |
| C4 | 86 | 53.62 | 9.96 | 17.24 |

[a]Peptide concentration prolonging clotting time twofold compared to the control in the prothrombin time (PT),activated partial thromboplastin time (APTT) and thrombin time (TT) test
[b]Value measured with isolated human fXa on Bz-lle-Glu-Gly-Arg-pNA chromogen substrate
[c]NA = inactive According to a recent publication [N. A. Prager et al., Circulation 92, 962 (1995)] not only thrombin but also factor Xa, entrapped in the thrombus/blood clot and liberated during dissolution, contributes to the initiation and maintenance of a new coagulation process through the activation of the [fVII+TF]-complex or factors V and VII, resp. Consequently, it is advantageous if the anticoagulants are able to inhibit factor Xa in addition to the inhibition of thrombin, particularly if this inhibition is extended to the clot-bound thrombin and factor Xa, too.

DISCLOSURE OF INVENTION

It is the objective of the present invention to prepare new peptide derivatives with improved anticoagulant activity compared to known compounds which exhibit anticoagulant activity at oral administration, too.

It was observed that the anticoagulant effect of BOC-D-Phe-Pro-Arg-H (C5) in TT and APTT tests is smaller than that of tripeptide aldehyde C1, but in PT test it is somewhat better, and it inhibits factor Xa with 10 times lower $IC_{50}$ than C1. It has been unexpectedly found that the substitution of Eoc-group for BOC-group in C5 positively modifies the anticoagulant effect of the peptide, because Eoc-D-Phe-Pro-Arg-H thus obtained shows higher effects than C5 in all three tests; in addition, its activity is higher than that of C1 not only in PT but in APTT test as well, while its fXa inhibiting effect is similar to that of BOC-peptide C5. The anticoagulant effect of Moc-D-Phe-Pro-Arg-H (C7) is similar to that of C6 Eoc-compound, but its fXa inhibiting effect is somewhat higher. These findings are demonstrated in Table 2.

TABLE 2

Anticoagulation (A) and fXa inhibiting effect (B) of peptide aldehydes with the structure R-D-Phe-Pro-Arg-H

| | | Peptide aldehyde | | | |
|---|---|---|---|---|---|
| | | A: IC$_{50}$, µM$^a$ | | | B |
| No. | R | TT | APTT | PT | IC$_{50}$, µM$^b$ |
| C1 | Me | 0.09 | 0.62 | 2.93 | 9.13 |
| C5 | Boc | 0.20 | 0.76 | 2.27 | 0.91 |
| C6 | Eoc | 0.13 | 0.38 | 1.91 | 0.92 |
| C7 | Moc | 0.20 | 0.29 | 1.96 | 0.13 |

$^a$Peptide concentration prolonging clotting time twofold compared to the control
$^b$Value measured with isolated human fXa on Bz-Ile-Glu-Gly-Arg-pNA chromogenic substrate It has also been found that even more effective anticoagulant compounds can be obtained if the N-terminal amino acid is changed from phenylalanine to 3-cyclobutylalanine, while when incorporating the homologous cyclobutyl-glycine into the N-terminal position the activity decreases. Apart from 3-cyclobutylalanine, substitution with 3-cyclopentylalanine also gives effective peptidylarginine aldehydes. It has also been observed that substitution of methoxycarbonyl or propoxycarbonyl groups for the N-terminal ethoxy-carbonyl group modifies the activity spectrum, i.e. the ratio of the measured activities in the individual tests.

MODE(S) FOR CARRYING OUT THE INVENTION

This invention relates to new peptide aldehyde derivatives of general formula (I), Q-D-Xaa-Pro-Arg-H    (I)

wherein
Q represents an acyl group of formula Q'—O—CO— where Q' is an alkyl group with 1–3 carbon atoms,
Xaa represents a 3-cyclobutyl-D-alanyl or 3-cyclopentyl-D-alanyl group,
Pro stands for an L-prolyl residue, and
Arg stands for an L-arginyl residue,
and their acid-addition salts formed with an organic or inorganic acid and pharmaceutical compositions containing the same.

The compounds of general formula (I), wherein Q, Q', Xaa, Pro and Arg have the same meaning as above, are prepared e.g. by condensing an acyldipeptide Q-D-Xaa-Pro with an L-arginine lactam, protected on the guanidino group with a benzyloxycarbonyl group, and reducing the obtained protected tripeptide lactam to the protected tripeptide aldehyde of the formula Q-D-Xaa-Pro-Arg(Z)-H, finally removing the Z group from the guanidino group of argi-nine, and isolating the peptide derivative of general for-mula (I) as its addition salt formed with an organic or inorganic acid.

The acyl-dipeptide, Q-D-Xaa-Pro, used as starting material, is prepared e.g. by acylating a D-Xaa amino acid with a Q' alkyl ester of chloroformic acid in a basic medium and the Q-D-Xaa acylamino acid thus obtained is coupled to L-proline.

Q-D-Xaa, required for the coupling to proline, can advantageously be prepared by acylating the racemic DL-Xaa compound, converting the DL-acylamino acid to its methyl ester and enzymatically resolving the Q-DL-Xaa-OMe racemic ester. The Q-D-Xaa-OMe thus obtained is then saponified to the needed Q-D-Xaa acylamino acid.

The compounds of general formula (I) of the invention, wherein Q, Xaa, Pro and Arg have the same meaning as above, exhibit strong anticoagulant activity both in vitro and in vivo and possess excellent bioavailability.

The in vitro anticoagulant effects of the compounds of general formula (I) was measured by the prothrombin time (PT), activated partial thromboplastin time (APTT) and thrombin time (TT) tests [D. Bagdy et al., Thromb. Haemost. 67, 325 (1992)]. The fxa-inhibiting effect of the compounds was also determined using the Bz-Ile-Glu-Gly-Arg-pNA chromogen substrate (see method M6).

The results obtained are presented in Table 3. The corresponding data of C1 thrombin inhibitor, C6 Eoc-D-Phe-compound and C8 Eoc-DL-Cba- analogue served as controls. In the Table the compounds are listed in the decreasing order of PT activity. The data definitely demonstrate the beneficial effect of the terminal Cba- and Cpa-moieties compared to the Phe (see 1, 4 and C6 compounds), and e.g. to the homologous cyclobutyl-glycine (see DL-series C8, C9 and C10 compounds).

TABLE 3

Anticoagulant (A) and fXa inhibiting (B) effect of the new peptidyl aldehydes (1–4, general formula Q-D-Xaa-Pro-Arg-H) and that of control compounds (C1, C6 and C8–C10) in the decreasing order of PT activity

| | | | A: IC$_{50}$, µM$^a$ | | | B: IC$_{50}$ |
|---|---|---|---|---|---|---|
| Exmpl$^b$ | Q | Xaa | PT | APTT | TT | nM$^c$ |
| Q-Xaa-Pro-Arg-H | | | | | | |
| 2 | Moc | D-Cba | 1.12 | 0.25 | 0.11 | 388 |
| 1 | Eoc | D-Cba | 1.15 | 0.35 | 0.11 | 40 |
| 4 | Eoc | D-Cpa | 1.41 | 0.24 | 0.10 | 27 |
| 3 | iPoc | D-Cba | 1.70 | 0.60 | 0.19 | 36 |
| Control compounds | | | | | | |
| C8 | Eoc | DL-Cba | 1.49 | 0.50 | 0.13 | 68 |
| C9 | Eoc | DL-Cpa | 1.90 | 0.48 | 0.26 | 43 |
| C6 | Eoc | D-Phe | 1.91 | 0.38 | 0.13 | 917 |
| C1 | D-MePhe | | 2.91 | 0.62 | 0.09 | 9133 |
| C10 | Eoc | DL-Cbg | 6.15 | 0.77 | 0.88 | 82 |

$^a$Peptide concentration inducing twofold thrombin time prolongation compared to control
$^b$Identical to Example number describing preparation of the respective compound
$^c$Value measured on substrate Bz-Ile-Glu-Gly-Arg-pNA with isolated human fXa (See methods M1–M5)

The inhibitory effect of the new compounds of the invention on plasmin (PL) as well as on plasmin formation induced by tissue plasminogen activator (tPA) and urokinase (UK) was examined by the fibrin-plate method [D. Bagdy et al.: Thromb. Haemost. 67, 325 (1992)]. Compounds C1 and C5 served as controls. It is well known that the antifibrinolytic effect of C1 proved to be insignificant in vivo, and it could be used as an adjuvant in dissolving the experimental thrombus, while the antifibrinolytic activity of C5 was well detectable in vivo [C. V. Jackson et al.: J. Cardiovasc. Pharmacol. 21, 587 (1993))]. In Table 4 the results obtained with the new compounds 1 and 2 as well as those with controls C1 and C5 are presented as an example.

In addition to the IC$_{50}$ values (columns A) the efficacy of the compounds related to C1 are also listed (columns B). The latter data indicate that similarly to compound C1 the antifibrinolytic activity of the new 1 and 2 compounds is moderate; their activity against the three enzymes tested is 3.2-4.5-39 times lower than that of compound C5.

TABLE 4

The inhibitory effect ($IC_{50}$) of the new peptidyl-arginine aldehydes of the invention and that of control compounds with similar structure on plasmin (PL) as well as on plasmin formation induced by tissue plasminogen activator (tPA) and urokinase (UK) studied by the fibrin-plate method[a].

| | Peptidyl arginine aldehyde A IC50 and B: relative efficiency[b] | | | | | |
|---|---|---|---|---|---|---|
| | PL | | tPA | | UK | |
| (Example)[c] | A | B | A | B | A | B |
| Eoc-D-Cba-Pro-Arg-H (1) | 39 | 1.4 | 27 | 4.9 | 120 | 0.7 |
| Moc-D-Cba-Pro-Arg-H (2) | 235 | 0.23 | 92 | 1.4 | 153 | 0.5 |
| Eoc-D-Cpa-Pro-Arg-H (3) | 98 | 0.55 | 38 | 3.5 | 46 | 1.8 |
| D-MePhe-Pro-Arg-H (C1) | 54 | 1.0 | 132 | 1.0 | 82 | 1.0 |
| Boc-D-Phe-Pro-Arg-H (C5) | 12 | 4.5 | 6 | 22.0 | 3 | 27.3 |

[a]$IC_{50}$ = peptide concentration ($\mu$M) where the hydrolysed area on the fibrin plate is reduced to 50% compared to the control
[b]Values related to the activity of C1 ($1/IC_{50}$ = 1)
[c]Identical to the example number describing the preparation of the respective compound The inhibitory effect of the new compounds of general formula (I) on clot-bound fXa and thrombin as well as on fibrin gel-bound thrombin is demonstrated in Table 5 with compounds 1–3; the respective values of C1 are used as controls. Plasma-clot was obtained by recalcificating platelet-rich human plasma, and fibrin gel by clotting human fibrinogen with human thrombin. For the activity measures of fXa and thrombin Z-D-Arg-Gly-Arg-pNA or Tos-Gly-Pro-Arg-pNA substrates were used in agreement with Methods M1–M3.

TABLE 5

Inhibitory effects ($IC_{50}$, $\mu$M) of new peptidyl-arginine aldehydes of the invention (1–3) and C1 as control compound on clot-bound fXa and thrombin as well as on fibrin-gel bound thrombin[a]

| | Peptidyl-arginine aldehyde | | |
|---|---|---|---|
| | Plasma clot | | Fibrin gel |
| (Number)[b] | fXa | Thrombin | Thrombin |
| Eoc-D-Cba-Pro-Arg-H (1) | 0.70 | 0.39 | 0.32 |
| Moc-D-Cba-Pro-Arg-H (2) | 0.39 | 0.68 | 0.64 |
| Eoc-D-Cpa-Pro-Arg-H (3) | 0.28 | 0.49 | 0.67 |
| D-MePhe-Pro-Arg-H (C1) | 1.12 | 0.38 | 0.30 |

[a]In determination of $IC_{50}$ values the activity of fXa and thrombin was measured on Moc-D-Chg-Gly-Arg-pNA or Tos-Gly-Pro-Arg-pNA substrates according to Methods M2 and M3
[b]The same as the number of the Example describing the new compound or control (C1)

These data show that Eoc-compounds 1 and 3 inhibit not only thrombin but plasma clot-bound fXa, too, with an $IC_{50}$ well below 1 micromole concentration.

The anticoagulant and platelet aggregation inhibiting effect of the compounds of general formula (I) was studied in New Zealand white rabbits ex vivo according to D. Bagdy et al. [Thromb. Haemost. 67, 357 (1992)]. The compounds were dissolved in buffered isotonic saline solution and administered i.v. (0,04–5.0 mg/kg) or by infusion (0.25–5.0 mg/kg/h) or subcutaneously (0.5–6.0 mg/kg) or p.o. (2.5–20 mg/kg). The effect of the compounds was detectable already within 30 minutes following p.o. administration, peak values were attained after 60–180 minutes and the therapeutic level was maintained dose-dependently for 3→6 hours.

The in vivo effect of ethoxycarbonyl-3-cyclobutyl-D-alanyl-L-prolyl-L-arginine aldehyde (1) is presented in detail in Tables 6 and 7. The corresponding values of C1 are listed as controls. The compound was administered p.o. in doses of 5 mg/kg. The blood samples drawn from the caudal vein in every 30–60 minutes were analysed. The whole blood clotting time (WBCT) and the inhibition of thrombin-induced blood platelet aggregation (PAI) were determined. The activated partial thromboplastin time (APTT) and the thrombin time (TT) in the citrate plasma obtained from the blood sample were also measured. The APTT and TT values are compiled in Table 6 and the WBCT and PAI values in Table 7.

The data of Tables 6 and 7 show that the new compound 1 has longer-lasting anticoagulant and antiaggregation effect than control C1.

TABLE 6

Anticoagulant effect of Eoc-D-Cba-Pro-Arg-H (1) and D-MePhe-Pro-Arg-H (C1) as control in rabbits at p.o. doses of 5 mg/kg in the APTT and TT tests characterised by relative clotting times[a]

| Time | Eoc-D-Cba-Pro-Arg-H | | D-MePhe-Pro-Arg-H | |
|---|---|---|---|---|
| min. | APTT | TT | APTT | TT |
| 0 | 1.0 | 1.0 | 1.0 | 1.0 |
| 30 | 1.73 ± 0.47 | 8.30 ± 5.67 | 1.27 ± 0.38 | 1.52 ± 0.17 |
| 45 | 1.84 ± 0.50 | 9.04 ± 5.50 | 1.30 ± 0.02 | 2.50 ± 0.44 |
| 60 | 1.94 ± 0.51 | 9.28 ± 5.45 | 1.37 ± 0.03 | 4.75 ± 1.38 |
| 90 | 1.92 ± 0.31 | 13.58 ± 5.43 | 1.45 ± 0.09 | 10.50 ± 4.59 |
| 120 | 1.75 ± 0.26 | 16.33 ± 5.89 | 1.43 ± 0.11 | 5.51 ± 3.59 |
| 180 | 1.59 ± 0.12 | 6.95 ± 3.73 | 1.39 ± 0.09 | 2.05 ± 0.38 |
| 240 | 1.38 ± 0.08 | 2.03 ± 0.42 | 1.31 ± 0.11 | 1.81 ± 0.39 |
| 300 | 1.28 ± 0.08 | 1.77 ± 0.50 | 1.25 ± 0.22 | — |

[a]Ratio of clotting times measured in treated and untreated animals. Therapeutic values are in italics.

TABLE 7

Anticoagulant and blood platelet aggregation inhibiting (PAI) effect of Eoc-D-Cba-Pro-Arg-H (1) and D-MePhe-Pro-Arg-H (C1) in rabbits at p.o. doses of 5 mg/kg in the WBCT test characterised by relative clotting time and percentual inhibition[a]

| Time | Eoc-D-Cba-Pro-Arg-H (1) | | D-MePhe-Pro-Arg-H (C1) | |
|---|---|---|---|---|
| min. | WBCT | PAI (%) | WBCT | PAI (%) |
| 0 | 1.0 | 1.0 | 1.0 | 1.0 |
| 30 | 1.52 ± 0.22 | 71.3 ± 16.6 | 1.07 ± 0.13 | 52.8 ± 14.7 |
| 45 | 1.58 ± 0.17 | 55.8 ± 17.4 | 1.26 ± 0.07 | 58.4 ± 15.6 |
| 60 | 1.88 ± 0.45 | 63.8 ± 21.2 | 1.55 ± 0.17 | 54.2 ± 11.6 |
| 90 | 1.73 ± 0.33 | 85.6 ± 10.0 | 1.61 ± 0.34 | 83.2 ± 8.9 |
| 120 | 1.98 ± 0.30 | 73.6 ± 19.1 | 1.45 ± 0.21 | 75.2 ± 12.3 |
| 180 | 1.43 ± 0.13 | 81.8 ± 11.6 | 1.44 ± 0.08 | 47.5 ± 20.9 |
| 240 | 1.12 ± 0.24 | 59.4 ± 19.1 | 1.22 ± 0.08 | 32.2 ± 16.0 |
| 300 | 1.18 ± 0.08 | 75.8 ± 11.8 | | |

[a]Ratio of clotting times measured in treated and untreated animals. Therapeutic values are in italics.

The compounds of the invention of general formula (I) are used for the treatment and prevention of the following diseases where thrombosis and/or hypercoagulability is involved: deep venous thrombosis, pulmonary embolism, arterial thrombosis, unstable angina, myocardial infarct, auricular fibrillation and thrombosis-based stroke. In atherosclerosis they may be used to prevent diseases of coronary arteries, thrombotic diseases of cerebral arteries as surgical prophylaxis of high risk patients or other surgical prophylaxis. They may be applied in the thrombolysis of percutaneous transluminal angioplastics for the prevention of reocclusion, for adjuvant therapy in nephrosis and in diseases with hypercoagulability: in malignant tumours and inflammation (e.g. arthritis) as well as in diabetes. They may be applied in cases where the administration of other anticoagulants fails to be effective or is contraindicated: e.g. lack of anti-thrombin-III in the case of heparin or heparin-induced thrombocytopenia (HIT), and e.g. pregnancy in the case of coumarins.

The compounds of the invention and their pharmaceutically acceptable salts are used for therapeutic purposes alone or preferably in the form of a pharmaceutical formulation. The invention also refers to these formulations.

The pharmaceutical formulations comprise an effective amount of a compound of general formula (I) or a pharmaceutically acceptable salt thereof and known pharmaceutically acceptable carriers, filling materials, diluents and/or other pharmaceutical excipients.

The above carriers, diluents or filling materials can be water, alcohols, gelatine, lactose, saccharose, starch, pectin, magnesium stearate, stearic acid, talcum, various oils of animal or plant origin, furthermore glycols, e.g. propylene glycol or polyethylene glycol. The pharmaceutical excipients can be preservatives, various natural or synthetic emulgeators, dispersing or wetting agents, colouring materials, flavouring agents, materials promoting disintegration and other materials improving the bioavailability of the active ingredient.

The pharmaceutical compositions of the invention can be prepared in usual formulations, such as oral compositions (administered through the mouth, such as tablets, capsules, powders, pills, dragees or granulates) as well as parenteral compositions (drugs administered by avoiding the gastrointestinal system such as injections, infusions, suppositories, plasters or ointments).

The therapeutic dose level of the compounds of the invention depends on the individual health status and age of the patient and may vary accordingly; consequently, its level is fixed by the physician designing treatment. In diseases where inhibition of the function and/or formation of thrombin is required for prophylactic or therapeutic purposes, a daily oral or parenteral (e.g. i.v.) dose of 0.01 to 1000 mg/kg body weight, preferably 0.25 to 20 mg/kg body weight, may be administered.

The compounds of general formula (I) of the invention, administered together with thrombolytic agents (e.g. tPA or urokinase), actively promote the dissolution of thrombi formed in arteries or veins and efficiently prevent their reformation. In such cases it is preferred to administer the compounds of the invention simultaneously with thrombolytic agents or immediately after thrombolytic treatment.

The following examples are illustrating but not limiting the scope of the invention.

The $R_f$ values recorded in the examples were determined by thin-layer chromatography, using silica gel as adsorbent (DC-Alufolien Kieselgel 60 $F_{254}$, Merck, Darmstadt), in the following developing solvents:

1. Ethyl acetate
2. Ethyl acetate-pyridine-acetic acid-water (480:20:6:11)
5. Ethyl acetate-pyridine-acetic acid-water (45:20:6:11)
6. Ethyl acetate-pyridine-acetic acid-water (240:20:6:11)
7. Ethyl acetate-pyridine-acetic acid-water (480:10:3:5.5)
9. Ethyl acetate-pyridine-acetic acid-water (120:20:6:11)
13. Ethyl acetate-n-butanol-acetic acid-water (1:1:1:1)

The capacity factors (k') specified in the examples were determined with the apparatus "Pharmacia LKB Analytical HPLC System Two" as follows:

Column: "VYDAC C-18 reversed phase: 10 mm, 300 A, 4×250 mm"
Buffer A: 0.1% trifluoroacetic acid in water
Buffer B: 0.1% trifluoroacetic acid in acetonitrile
Gradients applied at 1 ml/min. flow rate
I: 0–5 min. 0–25% B, then isocratic 25% B;
II: 0–30 min. 0–60% B.

Detection of peptide content of the eluates was performed by UV light at 214 nm. Sample concentration was 1 mg/ml buffer A, injection volume 25 µl.

The gradient applied in the HPLC analysis (I or II) is specified in brackets after the abbreviation at the individual steps of the examples.

The acylarginine aldehydes are present in equilibrium structures, i.e. in aldehyde, aldehyde hydrate and two aminocyclol forms. During HPLC analysis the aldehyde hydrate and one or both aminocyclol forms appear as separate peaks, consequently the acylarginine aldehydes described in the examples are specified by two or three k' values.

Mass spectrometry. The FAB positive ionisation measurements were performed in a Finnigan MAT 8430 apparatus. The samples were dissolved in m-nitrobenzyl-alcohol matrix and introduced directly into the ion source. In the spectrum of peptidyl-arginine aldehydes an additional molecule-ion was detectable, that of the addition compound formed with m-nitrobenzyl-alcohol (NBA): $[M+H]^+$ and $[M+H+NBA]^+$. In the examples the FAB spectral data were specified accordingly.

The ESI positive ionisation measurements were performed in a VG Quattro (Fisons) apparatus. The samples were dissolved in a mixture of acetonitrile-water (1:1) containing 1% (v/v) of formic acid and were introduced with a 10 ml sample-loop into the ion source at a flow rate of 15–25 ml/min.

The specific rotations ($[\alpha]_D$) were determined at 20° C.

EXAMPLE 1

Ethoxycarbonyl-3-cyclobutyl-D-alanyl-L-prolyl-L-arginine aldehyde (Eoc-D-Cba-Pro-Arg-H) hemisulfate Step 1: Ethoxycarbonyl-3-cyclobutyl-D-alanyl-L-prolyl-$N^G$-benzyloxy-carbonyl-L-arginine-lactam 3.28 g (8.4 mmol) of t-butoxycarbonyl-$N^G$-benzyloxy-carbonyl-L-arginine-lactame [S. Bajusz and co-workers: J. Med. Chem. 33, 1729 (1990)] is suspended in 8 ml of chloroform, then 10 ml of ethyl acetate, saturated with HCl gas (0.11–0.15 g/ml) is added with constant stirring and ice cooling. The reaction is followed by thin layer chromatography [$R_f(9)=0.91$ (Boc-compound); 0.07 (free compound)]. At the end the reaction mixture is diluted with 18 of ml diethyl ether, the crystalline mass formed is filtered, washed with 5 ml of acetone and 5 ml of diethyl ether, then dried in a vacuum desiccator over potassium hydroxide pellets. The $N^G$-benzyloxycarbonyl-L-arginine lactam hydrochloride obtained is dissolved in 8 ml of dimethylformamide, cooled to −20° C. and added to the mixed anhydride prepared below.

2.5 g (8 mmol) of ethoxycarbonyl-3-cyclobutyl-D-alanyl-L-proline (Example 1, Step E) is dissolved in 8 ml of dimethylformamide cooled to −20° C. With constant stirring 0.9 ml (8 mmol) of N-methyl-morpholine and 1.05 ml (8 mmol) of isobutyl chloroformate are introduced, then, after 10 min. stirring, the above-mentioned $N^G$-benzyloxy-carbonyl-L-arginine lactam hydrochloride solution and 2.35 ml (16.8 mmol) of triethyl amine. The reaction mixture is stirred for 30 minutes at −10° C., then for an hour at 0° C. The salts are filtered and discarded, the filtrate is diluted with 40 ml of benzene. The solution is washed with 3×10 ml of water, with 10 ml of 1M $KHSO_4$-solution and again with 3×10 ml of water, dried over anhydrous sodium sulphate and the solvent evaporated at a pressure of 2.0–2.5 kPa. The resulting product is applied onto a column made of 70 g Kieselgel 60 and eluted with ethyl acetate. The fractions containing pure material [$R_f(1)$=0.50] are pooled and the solvent evaporated at 2.0–2.5 kPa. The oily residue is rubbed with petroleum ether, filtered and dried.

Yield: 3.0 g (64%), $R_f(1)$=0.50, $[α]_D$=–47.4° (c=1, in THF).

The FAB mass spectra data confirm the expected structure (585 [M+H]$^+$).

Step 2: Ethoxycarbonyl-3-cyclobutyl-D-alanyl-L-prolyl-N$^G$-benzyloxy-carbonyl-L-arginine aldehyde 2.27 g (4.6 mmol) of ethoxycarbonyl-3-cyclobutyl-D-alanyl-L-prolyl-N$^G$-benzyloxy-carbonyl-L-arginine lactam (Example 1, Step 1) is dissolved in 15 ml of tetrahydrofuran and 3.6 mmol of lithium aluminium hydride, dissolved in tetrahydrofuran, is added at a temperature not higher than –50° C. with constant stirring. The progress of the reaction is monitored by thin-layer chromatography in solvent system (6) and more lithium aluminium hydride is added when it is needed. Pre-cooled 0.5M sulphuric acid solution is added to the reaction mixture with constant stirring and cooling until the solution reaches pH3. The resulting solution is extracted with 2×15 ml of n-hexane, then with 3×20 ml of methylene chloride. The methylene chloride extracts are pooled, washed with 3×15 ml of water, 15 ml of cold 5% NaHCO$_3$-solution, then again with 15 ml of water, dried over anhydrous sodium sulphate, and the solvent is evaporated at a pressure of 2.0–2.5 kPa. The residue is dissolved in 10 ml of benzene and precipitated with cyclohexane. After filtering and drying the product weighs 1.8 g (65%). $R_f(6)$=0.30, $[α]_D$=–30.8° (c=1, in tetrahydrofuran).

The FAB mass spectrum confirms the assumed structure (587 [M+H]$^+$).

Step 3: Ethoxycarbonyl-3-cyclobutyl-D-alanyl-L-prolyl-L-arginine aldehyde hemisulfate 1.58 g (2,7 mmol) of ethoxycarbonyl-3-cyclobutyl-D-alanyl-L-prolyl-N$^G$-benzyloxy-carbonyl-L-arginine aldehyde (Example 1, Step 2) is dissolved in 14 ml of ethanol, 2,7 ml of 0.5M sulphuric acid, 3.2 ml of water and then 0.17 g of Pd/C catalyst, suspended in 6 ml of ethanol, are added and the system is hydrogenated at 10° C. The reaction, whose progress is monitored by thin-layer chromatography, is complete in 15 minutes. The catalyst is filtered off and the solution is concentrated to a volume of 7–9 ml at a pres-sure of 2.0–2.5 kPa. The residue is diluted with 20 ml of water, extracted with 6 ml of methylene chloride, and the aqueous solution is allowed to stand at room temperature for 24 hours. The pH is then adjusted to 3.5 with Dowex AG 1-X8 resin in OH-cycle and the solution freeze-dried.

Yield: 1.0 g (78%), $R_f(5)$=0.44, $[α]_D$=–75.5° (c=1, in water). HPLC(I): k'=5.53; 6.20 and 7.17.

The FAB mass spectrum confirms the assumed structure (453 [M+H]$^+$).

The starting material can be prepared as follows:

Ethoxycarbonyl-3-cyclobutyl-D-alanyl-L-proline
(Eoc-D-Cba-Pro)

Step A: Ethoxycarbonyl-3-cyclobutyl-DL-alanine 10 g (70 mmol) of 3-cyclobutyl-DL-alanine [A. Burger et al., J. Med. Chem. 6, 221 (1963)] is dissolved, in 70 ml of 2M NaOH solution, cooled to +5° C. and 11.1 ml (116.2 mmol) of ethyl chloroformate is added in drops with constant stirring. Stirring is continued for 2 hours at this temperature, and for further 2 hours at room temperature. The reaction mixture is then washed with 20 ml of diethyl ether and after acidifying the solution to pH1 extracted with 3×20 ml of ethyl acetate. The pooled extracts are washed with brine, dried over anhydrous sodium sulphate and the solvent is evaporated at a pressure of 2.0–2.5 kPa. The resulted oil is considered to be the pure product [Yield: 13.1 g (87%), $R_f(7)$=0.8] and is used without further treatment in the next step.

Step B: Methyl Ethoxycarbonyl-3-cyclobutyl-DL-alaninate 11 g (51 mmol) of ethoxycarbonyl-3-cyclobutyl-DL-alanine (Example 1, Step A) is dissolved in 100 ml of methanol, cooled to –15° C. and 10 ml (137 mmol) of thionyl chloride is added at constant stirring. Stirring is continued without further cooling. When the reaction mixture reaches room temperature, stirring is continued for further 2 hours. The solution is then evaporated at a pressure of 2.0–2.5 kPa. The residual oil is dissolved in 40 ml of ethyl acetate, washed with 10 ml of 1N HCl, 2×10 ml of 5% NaHCO$_3$ and 2×10 ml of water, dried over anhydrous sodium sulphate and evaporated to dryness at a pressure of 2.0–2.5 kPa. The residue is considered to be pure [yield: 10.8 g (92%), $R_f(1)$=0.85; $R_f(6)$=0.65] and is used without further treatment in the next step.

Step C: Methyl Ethoxycarbonyl-3-cyclobutyl-D-alaninate

The enzymatic hydrolysis of acyl amino acid methyl esters can be performed at pH=7.5 in an automatic titrator which has two reaction vessels (one with a volume of 100 ml and another with 250 ml). The reagent is 1M NaOH solution.

10.8 g (47 mmol) of methyl ethoxycarbonyl-3-cyclobutyl-DL-alaninate (synthesised in Step B) is dissolved in 20 ml of benzene in the 250 ml vessel of the titrator. 100 ml of water is added and the pH of the solution is adjusted to 7.5 with 1M NaOH under stirring. 40 mg of enzyme [Subtilisin Carlsberg, Protease, Type VIII (Sigma)] is added, the pH readjusted to 7.5 and kept at this value during titration. The enzymatic hydrolysis is complete in 3 hours. The phases are separated. From the aqueous phase pure ethoxy-carbonyl-3-cyclobutyl-L-alanine can be isolated. The benzene phase is washed with 2×10 ml of 5% NaHCO$_3$ and 2×10 ml of water, dried over anhydrous sodium sulphate and evaporated at a pressure of 2.0–2.5 kPa. The resulting yellowish oil is considered to be pure and used without further treatment in the next step.

Step D: Ethoxycarbonyl-3-cyclobutyl-D-alanine

The oily product of Step C is dissolved in 20 ml of ethanol, and 10 ml of 2.5M NaOH solution is added. The mixture is stirred for 2 hours at room temperature and evaporated at a pressure of 2.0–2.5 kPa. The residue is dissolved in 30 ml of water, washed with 10 ml of diethyl ether, acidified to pH=1 with 3M hydrochloric acid and extracted with 3×10 ml of ethyl acetate. The pooled organic extracts are washed with brine, dried over anhydrous sodium sulphate and evaporated at a pressure of 2.0–2.5 kPa. Yield: 4.3 g (90%) of an oily product [$R_f(2)$=0.8], of which the greater part is used in the next step, the remainder is converted to crystalline salt as follows.

0.43 g (2 mmol) of oily ethoxycarbonyl-3-cyclobutyl-D-alanine (Example 1, Step D.) is dissolved in 10 ml of diethyl ether and 0.23 ml (2.1 mmol) of cyclohexyl amine is added. The separated crystals are filtered, washed with diethyl ether and dried in a vacuum desiccator.

Yield: 0.57 g (90%). M.p.: 129–131° C., $[α]_D$=3.93° (c=1, in methanol). Analysis for $C_{16}H_{30}N_2O_4$ (314.42): Calculated: C%=61.12; H%=9.62; N%=8.91 Found: C%=61.30; H%=9.80; N%=8.60

Step E: Ethoxycarbonyl-3-cyclobutyl-D-alanyl-L-proline 3.7 g (17.2 mmole) of ethoxycarbonyl-3-cyclobutyl-D-alanine (Example 1, Step D) is dissolved in 60 ml of tetrahydrofuran, cooled to 0° C., then 4.85 g (24.5 mmol) of 2,4,5-trichlorophenol and 5.06 g (24.5 mmol) of dicyclohexyl-carbodiimide are added. The reaction mixture is stirred at room temperature for 2 hours, filtered from the separated dicyclohexylurea and washed with tetrahydrofuran. The filtrate and the washings are pooled and evaporated at a pressure of 2.0–2.5 kPa. The residue is dissolved in 25 ml of diethyl ether-petroleum ether mixture (1:1), the insoluble dicyclohexylurea is filtered off and the filtrate is evaporated again [the filtered dicyclohexylurea amounts to 4.9 g (89%) and 0.6 g (11%), respectively]. The oily 2,4,5-trichlorophenyl ethoxycarbonyl-3-cyclobutyl-D-alaninate is dissolved in 40 ml of pyridine and 2.12 g (18.4 mmol) of finely pulverised L-proline is added together with 3.43 ml (24.6 mmol) of triethyl amine. The reaction mixture is stirred at room temperature for 3 hours, then evaporated at a pressure of 2.0–2.5 kPa. The residue is distributed between 50 ml of ethyl acetate and 50 ml of 1M HCl. The organic phase is washed first with 10 ml of 1M HCl then with 2×10 ml of water and is extracted with 3×100 ml of 5% $NaHCO_3$. The pooled hydrocarbonate extracts are acidified to pH3 with 6M HCl and extracted with 3×20 ml of diethyl ether. The ethereal extracts are pooled, washed acid-free with water, dried over anhydrous sodium sulphate and evaporated to dryness.

Yield: 3.2 g (60%) oil. $R_f(6)$=0.49.

The FAB mass spectrum (313 $[M+H]^+$) confirms the assumed structure.

EXAMPLE 2

Methoxycarbonyl-3-cyclobutyl-D-alanyl-L-prolyl-$N^G$-benzyloxycarbonyl-L-arginine aldehyde (MOC-D-Cba-Pro-Arg-H) hemisulfate Step 1: Methoxycarbonyl-3-cyclobutyl-D-alanyl-L-prolyl-$N^G$-benzyloxy-carbonyl-L-arginine lactam Starting with 1.64 g (4.2 mmol) of t-butoxycarbonyl-$N^G$-benzyloxycarbonyl-L-arginine lactam [S. Bajusz et al., J. Med. Chem. 33, 1729 (1990)] and 1.25 g (4.0 mmol) of methoxycarbonyl-3-cyclobutyl-D-alanyl-L-proline (Example 2, Step C), the coupling of these components and the chromatographic purification of the end-product is performed according to Example 1, Step 1 using proportional quantities of reagents and solvents. The fractions containing pure end-product [$R_f(1)$=0] are pooled and evaporated at a pressure of 2.0–2.5 kPa. The residue is rubbed with petroleum ether, filtered and dried in a desiccator over paraffin turnings and phosphorus pentoxide.

Yield: 1.15 g (50%). $R_f(2)$=0.45–0.47. $[\alpha]_D$=-43.5° (c=1, in tetrahydrofuran).

The FAB mass spectrum (571 $[M+H]^+$, 724 $[M+H+NBA]^+$) confirms the assumed structure.

Step 2: Methoxycarbonyl-3-cyclobutyl-D-alanyl-L-prolyl-$N^G$-benzyloxycarbonyl-L-arginine aldehyde 1.06 g (1.8 mmol) of methoxycarbonyl-3-cyclobutyl-D-alanyl-L-prolyl-L-arginine lactam (Example 2, Step 1) is reduced according to the method described in Example 1, Step 2, using proportional quantities of reagents and solvents.

Yield: 0.76 g (73%). $R_f(9)$=0.47. $[\alpha]_D$=-37.5° (c=1 in tetrahydrofuran).

The FAB mass spectrum (573 $[M+H]^+$, 726 $[M+H+NBA]^+$) confirms the assumed structure.

Step 3: Methoxycarbonyl-3-cyclobutyl-D-alanyl-L-prolyl-$N^G$-benzyloxycarbonyl-L-arginine aldehyde hemisulfate 0.69 g (1.2 mmol) of methoxycarbonyl-3-cyclobutyl-D-alany-L-prolyl-$N^G$-benzyloxycarbonyl-L-arginine aldehyde (Example 2, Step 2) is subjected to hydrogenolysis according to the method described in Example 1, Step 3, using proportional quantities of reagents and solvents.

Yield: 0.53 g (91%). 15 HPLC(II): k'=4.74; 5.47 and 5.82. $[\alpha]_D$=-60.9° (c=1, in water).

The FAB mass spectrum (439 $[M+H]^+$, 592 $[M+H+NBA]^+$ confirms the assumed structure.

The starting material can be prepared as follows:

Methoxycarbonyl-3-cyclobutyl-D-alanyl-L-proline (MOC-D-Cba-Pro)

Step A: Methoxycarbonyl-3-cyclobutyl-DL-alanine 4.3 g (30 mmol) of 3-cyclobutyl-DL-alanine [A. Burger et al., J. Med. Chem. 6, 221 (1963)] is dissolved in 15 ml of 2M NaOH solution, cooled to 0° C. and simultaneously 16.5 ml of 2M NaOH solution and 2.55 ml (33 mmol) of methyl chloroformate are added with vigorous stirring. Stirring is continued at this temperature for 30 minutes and at room temperature for 2 hours. The reaction mixture is diluted with 40 ml of water, extracted with 10 ml of diethyl ether, then acidified to pH3 with 3M HCl. The product is extracted with ethyl acetate (4×20 ml), the extracts are pooled, washed with 20 ml of water, dried over anhydrous sodium sulphate and evaporated at a pressure of 2.0–2.5 kPa. The oily residue [5.3 g (88%), $R_f(7)$=0.61] is used without further purification in the next step.

Step B: Methoxycarbonyl-3-cyclobutyl-D-alanine 5.03 g (25 mmol) of methoxycarbonyl-3-cyclobutyl-DL-alanine (Example 2, Step A) is treated according to the method described in Example 1, Steps B–D, using proportional quantities of reagents and solvents.

Yield: 2.22 g (11 mmol) oily product. [$R_f(7)$=0.61].

Step C: Methoxycarbonyl-3-cyclobutyl-D-alanyl-L-proline 1.21 g (6 mmol) of methoxycarbonyl-3-cyclobutyl-D-alanine (Example 2, Step B) is treated according to the method described in Example 1, Step E, using proportional quantities of reagents and solvents. Yield: 1.6 g (5.4 mmol, 90%) oily product [$R_f(9)$=0.48], the larger part of which is used directly in Step 1, while the remainder is converted to a crystalline salt as follows.

0.30 g (1 mmol) of oily methoxycarbonyl-3-cyclobutyl-D-alanyl-L-proline is dissolved in 5 ml of diethyl ether and 0.21 ml (1.05 mmol) of dicyclohexyl amine is added. The separated crystals are filtered off, washed with diethyl ether and dried in a vacuum desiccator.

Yield: 0.43 g (90%). M.p.: 149.5–164° C. Analysis for $C_{24}H_{45}N_3O_5$ (479.64) Calculated: C%=65.10; H%=9.46; N%=8.76; Found: C%=60.4; H%=8.98; N%=10.47.

EXAMPLE 3

Isopropoxycarbonyl-3-cyclobutyl-D-alanyl-L-prolyl-L-arginine aldehyde (iPoc-D-Cba-Pro-Arg-H) hemisulfate Step 1: Isopropoxycarbonyl-3-cyclobutyl-D-alanyl-L-prolyl-$N^G$-benzyloxycarbonyl-L-arginine lactam Starting with 0.43 g (1.1 mmol) of t-butoxycarbonyl-$N^G$-benzyloxy-carbonyl-L-arginine lactam [S. Bajusz et al., J. Med. Chem. 33, 1729 (1990)] and 0.33 g (1 mmol) of isopropoxycarbonyl-3-cyclobutyl-D-alanyl-L-proline (Example 3, Step C) the components are coupled and the product chromatographically purified according to the method described in Example 1, Step 1, using proportional quantities of reagents and solvents The fractions containing pure end-product [$R_f(1)$=0.55] are pooled, evaporated at a pressure of 2.0–2.5 kPa, the residue is rubbed with petroleum ether, filtered and dried in a desiccator.

Yield: 0.3 g (50%), $R_f(1)$=0.55.

The FAB mass spectrum (599 $[M+H]^+$, 752 $[M+H+NBA]^+$) confirms the assumed structure.

Step 2: Isopropoxycarbonyl-3-cyclobutyl-D-alanyl-L-prolyl-N$^G$-benzyloxycarbonyl-L-arginine aldehyde 0.26 g (0.43 mmol) of isopropoxycarbonyl-3-cyclobutyl-D-alanyl-L-prolyl-N$^G$-benzyloxycarbonyl-L-arginine lactam (Example 2, Step 1) is hydrogenated according to the method described in Example 1, Step 2, using proportional quantities of reagents and solvents.

Yield: 0.15 g. R$_f$(6)=0.30.

The FAB mass spectrum (601 (M+H]$^+$, 754 [M+H+NBA]$^+$) confirms the assumed structure.

Step 3: Isopropoxycarbonyl-3-cyclobutyl-D-alanyl-L-prolyl-L-arginine aldehyde hemisulfate 0.13 g (0.2 mmol) of isopropoxycarbonyl-3-cyclobutyl-D-alanyl-L-prolyl-N$^G$-benzyloxycarbonyl-L-arginine aldehyde (Example 2, Step 2) is treated according to the method described in Example 1, Step 3, using proportional quantities of reagents and solvents.

Yield: 0.07 g (75%).

HPLC(I): k'=3.69; 4.15 and 5.04.

The FAB mass spectrum (467 [M+H]$^+$, 620 [M+H+NBA]$^+$) confirms the assumed structure.

The starting material can be prepared as follows:

Isopropoxycarbonyl-3-cyclobutyl-D-alanyl-L-proline (iPoc-D-Cba-Pro)

Step A: 3-Cyclobutyl-D-alanine

To 1.0 g (5 mmol) of methoxycarbonyl-3-cyclobutyl-D-alanine (Example 2, Step 2) 10 ml of 6M HCl is added and heated to reflux for 3 hours. The solution is evaporated at a pressure of 2.0–2.5 kPa, the residue is dissolved in 5 ml of water and evaporated to dryness and this process is repeated. The traces of water can be removed by azeotropic distillation with ethanol-benzene mixture. The residual oil is dissolved in 10 ml of ethanol and 5 mmol of 1,2-epoxy-propane is added. After cooling the precipitate is filtered off, the solid is washed with diethyl ether and dried.

Yield: 0.65 g (90%) of 3-cyclobutyl-D-alanine. R$_f$(13)= 0.65. [α]$_D$=−34.7° (c=1, in 1M HCl). Analysis for C$_7$H$_{13}$NO$_2$: Calculated: C%=58.71; H%=9.15; N%=9.78; Found: C%=58.70; H%=9.30; N%=9.50.

Step B: Isopropoxycarbonyl-3-cyclobutyl-D-alanine 0.57 g (4 mmol) of 3-cyclobutyl-D-alanine is dissolved in 8 ml 1:1 mixture of 1M NaOH solution and dioxane. The mixture is cooled to 0° C. and simultaneously 4 ml of 1M NaOH solution and 4 ml of isopropyl chloroformate (conc. 1M in toluene) solution are added with vigorous stirring. The reaction mixture is stirred for 1 hour at this temperature and for 5 hours at room temperature.

Dioxane and toluene are distilled off at a pressure of 2.0–2.5 kPa. The remaining aqueous solution is washed with 5 ml of diethyl ether, then acidified to pH3 with 1M KHSO$_4$ solution. The emulsion is extracted with 3×5 ml of ethyl acetate, the pooled extracts are washed with water and dried over anhydrous sodium sulphate. After evaporating at a pressure of 2.0–2.5 kPa the yield is 0.83 g (90%).

R$_f$(6)=0.60; [α]$_D$=+9.5° (c=0.5, in methanol).

Step C: Isopropoxycarbonyl-3-cyclobutyl-D-alanyl-L-proline 0.46 g (2 mmol) of isopropoxycarbonyl-3-cyclobutyl-D-alanine (Example 3, Step B) is treated according to the method described in Example 1, Step E, using proportional quantities of reagents and solvents.

Yield: 1.3 g (4.35 mmol, 87%) oil. R$_f$(2)=0.40.

The FAB mass spectrum (327 [M+H]$^+$) confirms the assumed structure.

EXAMPLE 4

Ethoxycarbonyl-3-cyclopentyl-D-alanyl-L-prolyl-L-arginine aldehyde (Eoc-D-Cpa-Pro-Arg-H) hemisulfate Step 1: Ethoxycarbonyl-3-cyclopentyl-D-alanyl-L-prolyl-N$^G$-benzyl-oxycarbonyl-L-arginine lactam 2.93 g (7.5 mmol) of t-butoxycarbonyl-N$^G$-benzyloxycarbonyl-L-arginine lactam [S. Bajusz et al., J. Med. Chem. 33, 1729 (1990)] and 2.3 g (7.1 mmol) of ethoxycarbonyl-3-cyclopentyl-D-alanyl-L-proline (Example 4, Step C) are treated according to the method described in Example 1, Step 1, using proportional quantities of reagents and solvents. The fractions containing pure end-product [R$_f$(1)= 0.55] are pooled, evaporated at a pressure of 2.0–2.5 kPa, the remaining oil is rubbed with n-hexane, filtered off, washed with n-hexane and dried in a vacuum desiccator.

Yield: 2.5 g (59%). R$_f$(1)=0.55, [α]$_D$=−48.6° (c=1, in tetrahydrofuran).

The FAB mass spectrum (599 [M+H]$^+$, 752 [M+H+NBA]$^+$) confirms the assumed structure.

Step 2: Ethoxycarbonyl-3-cyclopentyl-D-alanyl-L-prolyl-N$^G$-benzyloxycarbonyl-L-arginine aldehyde 2.34 g (3.9 mmol) of ethoxycarbonyl-3-cyclopentyl-D-alanyl-L-prolyl-N$^G$-benzyloxycarbonyl-L-arginine lactam (Example 4, Step 1) is reduced according to the method described in Example 1, Step 2, using proportional quantities of reagents and solvents.

Yield: 1.75 g (74.7%). R$_f$(6)=0.42, [α]$_D$=−34.4° (c=1, in tetrahydrofuran).

The FAB mass spectrum (601 [M+H]$^+$, 754 [M+H+NBA]$^+$) confirms the assumed structure.

Step 3: Ethoxycarbonyl-3-cyclopentyl-D-alanyl-L-prolyl-L-arginine aldehyde hemisulfate 1.59 g (2.65 mmol) of ethoxycarbonyl-3-cyclopentyl-D-alanyl-L-prolyl-N-benzyloxycarbonyl-L-arginine aldehyde (Example 4, Step 2) is hydrogenated according to the method described in Example 1, Step 3, using proportional quantities of reagents and solvents.

Yield: 1.13 g (83%). R$_f$(3)=0.37. [α]$_D$=−34.4° (c=1, in water). HPLC(I): k'=4.76; 5.40 and 7.32.

The FAB mass spectrum (467 [M+H]$^+$, 620 [M+H+NBA]$^+$) confirms the assumed structure.

The starting material can be prepared as follows:

Ethoxycarbonyl-3-cyclopentyl-D-alanyl-L-proline (Eoc-D-Cpa-Pro)

Step A: Ethoxycarbonyl-3-cyclopentyl-DL-alanine 7.87 g (50 mmol) of 3-cyclopentyl-DL-alanine [P. R. Pal et al., J. Am. Chem. Soc., 78, 5116 (1956)] is treated according to the method described in Example 1, Step A, using proportional quantities of reagents and solvents, with the exception that the product from the reaction mixture is extracted with 2×50 ml diethyl ether, dried over anhydrous sodium sulphate and evaporated at a pressure of 2.0–2.5 kPa. Yield: 10.55 g (98%) of white, amorphous powder. [R$_f$(2)= 0.84] which is used without further purification in the next step.

Step B: Ethoxycarbonyl-3-cyclopentyl-D-alanine 7.8 g (34 mmol) of ethoxycarbonyl-3-cyclopentyl-DL-alanine (Example 4, Step A) is treated according to the method described in Example 1, Steps B,C,D using proportional quantities of reagents and solvents. Yield: 3.45 g (88.6%) of an oil [R$_f$(6)=0.062], the larger part of which is used directly in Step C. The remainder is converted to a crystalline salt as follows:

0.46 g (2 mmol) of oily ethoxycarbonyl-3-cyclopentyl-D-alanine is dissolved in 10 ml of diethyl ether and 0.42 ml (2.1 mmol) of dicyclohexyl amine is added. The precipitate is filtered off, washed with diethyl ether and dried in a vacuum desiccator.

Yield: 0.74 g (90%) crystalline salt. M.p.: 138–140° C., [α]$_D$=−1.5° (c=1, methanol). Analysis for C$_{23}$H$_{42}$N$_2$O$_4$ (410.58): Calculated: C%=67.28; H%=10.31; N%=6.81; Found: C%=67.40; H%=10.40; N%=6.80.

Step C: Ethoxycarbonyl-3-cyclopentyl-D-alanyl-L-proline 2.43 g (10.5 mmol) of ethoxycarbonyl-3-cyclopentyl-D-alanine (Example 4, Step B) is treated according to the method described in Example 1, Step E, using proportional quantities of reagents and solvents. The resulting 2,4,5-trichlorophenylester is coupled with 1.15 g (10 mmol) of L-proline which yields 2.3 g (71%) of an oily product. $R_f(6)=0.53$.

The FAB mass spectrum (327 [M+H]$^+$) confirms the assumed structure.

Synthesis of Control Compounds

Synthesis 1

Ethoxycarbonyl-3-phenyl-D-alanyl-L-prolyl-L-arginine aldehyde (Eoc-D-Phe-Pro-Arg-H) hemisulfate Step 1: Ethoxycarbonyl-3-phenyl-D-alanyl-L-prolyl-N$^G$-benzyloxycarbonyl-L-arginine lactam Starting with 2.3 g (5.8 mmol) of t-butoxycarbonyl-N$^G$-benzyloxycarbonyl-L-arginine lactam [S. Bajusz et al. J. Med. Chem. 33, 1729 (1990)] and 1.67 g (5 mmol) of ethoxycarbonyl-3-phenyl-D-alanyl-L-proline (Synthesis 1, Step C), the coupling of the components and the purification of the product is performed according to the method described in Example 1, Step 1, using proportional quantities of reagents and solvents. The fractions containing pure product [$R_f(1)=0.37$] are pooled and evaporated at a pressure of 2.0–2.5 kPa. The residue is dried in a vacuum desiccator. Yield: 1.18 g (60%) of an oil.

The FAB mass spectrum (607 [M+H]$^+$) confirms the assumed structure.

Step 2: Ethoxycarbonyl-3-phenyl-D-alanyl-L-prolyl-N$^G$-benzyloxycarbonyl-L-arginine aldehyde 0.9 g (1.5 mmol) of ethoxycarbonyl-3-phenyl-D-alanyl-L-prolyl-N$^G$-benzyloxycarbonyl-L-arginine lactam (Synthesis 1, Step 1) is reduced according to the method described in Example 1, Step 2, using proportional quantities of reagents and solvents.

Yield: 0.33 g (36%). $R_f(1)=0.16$

Step 3: Ethoxycarbonyl-3-phenyl-D-alanyl-L-prolyl-L-arginine aldehyde hemisulfate 0.33 g (0.54 mmol) of ethoxycarbonyl-3-phenyl-D-alanyl-L-prolyl-N$^G$-benzyloxyarbonyl-L-arginine aldehyde (Synthesis 1, Step 2) is treated according to the method described in Example 1, Step 3, using proportional quantities of reagents and solvents.

Yield: 0.26 g (92%). HPLC(I): k'=4.00; 4.45 and 5.45.

The FAB mass spectrum (475 [M+H]$^+$, 628 [M+H+NBA]$^+$) confirms the assumed structure.

The starting material can be prepared as follows:

Ethoxycarbonyl-3-phenyl-D-alanyl-L-proline (Eoc-D-Phe-Pro)

Step A: Ethoxycarbonyl-3-phenyl-D-alanine 16.5 g (0.1 mole) of 3-phenyl-D-alanine is treated according to the method described in Example 1, Step A, using proportional quantities of reagents and solvents with the exception that after evaporating the solvent from the ethyl acetate solution of the end product, the resulting oil is dried in a vacuum desiccator.

Yield: 14.6 g (55%). $R_f(9)=0.70$.

Step B: Ethoxycarbonyl-3-phenyl-D-alanine N-hydroxy-succinimidate 14.5 g (55.4 mmol) of ethoxycarbonyl-3-phenyl-D-5 alanine (Synthesis 1, Step A) and 6.4 g (56 mmol) of N-hydroxy-succinimide are dissolved in 60 ml of tetrahydrofuran. The solution is cooled to 0° C. and 11.5 g (56 mmol) of dicyclohexyl-carbodiimide is added while stirring. Stirring is continued at this temperature for 10 hours, then the mixture is filtered and the filtrate evaporated at a pressure of 2.0–2.5 kPa. The residue is crystallised from benzene. The crystals are filtered, washed with benzene and diethyl ether and dried in a vacuum desiccator.

Yield: 11.3 g (60%). $R_f(10)=0.53$, $[\alpha]_D=+58.1°$ (c=1, dimethylformamide).

The FAB mass spectrum (335 [M+H]$^+$) confirms the assumed structure.

Analysis for $C_{16}H_{18}N_2O_6$ (334.33): Calculated: C%=57.48; H%=5.42; N%=8.30; Found: C%=57.40; H%=5.40; N%=8.30.

Step C: Ethoxycarbonyl-3-phenyl-D-alanyl-L-proline 3.34 g (10 mmol) of ethoxycarbonyl-3-phenyl-D-alanine hydroxysuccinimidate (Synthesis 1, Step B) is dissolved in 15 ml of pyridine and 1.15 g (10 mmol) of L-proline and 1.4 ml (10 mmol) of triethylamine are added. The reaction mixture is stirred at room temperature for 10 hours, then evaporated at a pressure of 2.0–2.5 kPa. The residue is distributed between 30 ml 5% NaHCO$_3$ solution and 10 ml of diethyl ether. The aqueous phase is washed with 3×5 ml of diethyl ether, the pooled organic washings are extracted with 5 ml 5% NaHCO$_3$-solution. The bicarbonate phases are pooled, acidified with 1M KHSO$_4$ solution to pH3 and extracted with 3×10 ml of ethyl acetate. The pooled organic extracts are dried over anhydrous sodium sulphate and evaporated at a pressure of 2.0–2.5 kPa. The oily residue is crystallised with diethyl ether, the crystals are filtered, washed with diethyl ether and dried in a vacuum desiccator.

Yield: 2.6 g (77%). M.p.: 141–143° C., $R_f(6)=0.40$.

The FAB mass spectrum (335 [M+H]$^+$) confirms the assumed structure.

Analysis for $C_{17}H_{22}N_2O_5$ (334.33): Calculated: C%=61.06; H%=6.63; N%=5.38; Found: C%=61.10; H%=6.70; N%=8.1.

Synthesis 2

Methoxycarbonyl-3-phenyl-D-alanyl-L-prolyl-L-arginine aldehyde (Moc-D-Phe-Pro-Arg-H) hemisulfate Step 1: Methoxycarbonyl-3-phenyl-D-alanyl-L-prolyl-N$^G$-benzyloxycarbonyl-L-arginine lactam Starting with 4.1 g (10.5 mmol) of t-butoxycarbonyl-N$^G$-benzyloxycarbonyl-L-arginine lactam [S. Bajusz et al., J. Med. Chem. 33, 1729 (1990)] and 2.88 g (9 mmol) of methoxycarbonyl-3-phenyl-D-alanyl-L-proline (Synthesis 1, Step C) the coupling is performed according to the method described in Example 1, Step 1 using proportional quantities of reagents and solvents. The crude product is purified by crystallising from cyclohexane.

Yield: 4.65 g (86%). M.p.: 72–82.7° C. $R_f(2)=0.56$. $[\alpha]_D=+72.9°$ (c=1, in tetrahydrofuran).

The FAB mass spectrum (593 [M+H]$^+$, 746 [M+H+NBA]$^+$) confirms the assumed structure.

Step 2: Methoxycarbonyl-3-phenyl-D-alanyl-L-prolyl-N$^G$-benzyloxycarbonyl-L-arginine aldehyde 4.13 g (7 mmol) of methoxycarbonyl-3-phenyl-D-alanyl-L-prolyl-N$^G$-benzyloxycarbonyl-L-arginine lactam (Synthesis 2, Step 1) is reduced according to the method described in Example 1, Step 2, using proportional quantities of reagents and solvents with the exception that after evaporating the methylene chloride solvent the oily end product is crystallised with diethyl ether. The crystals are filtered, washed with diethyl ether and dried in a vacuum desiccator.

Yield: 3.06 g (74%). M.p.: 103–107° C. $R_f(6)=0.44$. $[\alpha]_D=-69°$ (c=1, in tetrahydrofuran).

The FAB mass spectrum (595 $[M+H]^+$, 748 $[M+H+NBA]^+$) confirms the assumed structure.

Step 3: Methoxycarbonyl-3-phenyl-D-alanyl-L-prolyl-L-arginine aldehyde hemisulfate 2.68 g (4.5 mmol) of methoxycarbonyl-3-phenyl-D-alanyl-L-prolyl-$N^G$-benzyloxycarbonyl-L-arginine aldehyde (Synthesis 2, Step 2) is treated according to the method described in Example 1, Step 2, using proportional quantities of reagents and solvents.

Yield: 2.15 g (94%). $[\alpha]_D=-87.6°$ (c=1, in water). HPLC (I): k'3.3; 3.57 and 4.09.

The FAB mass spectrum (461 $[M+H]^+$, 614 $[M+H+NBA]^+$) confirms the assumed structure.

The starting material can be prepared as follows:

Methoxycarbonyl-3-phenyl-D-alanyl-L-proline
(Moc-D-Phe-Pro)

Step A: Methoxycarbonyl-3-phenyl-D-alanine dicyclohexylamine salt 5 g (30 mmol) of D-phenylalanine is dissolved in 15 ml of 2M NaOH solution, cooled to 0° C. and, simultaneously, 16.5 ml of 2M NaOH solution and 2.55 ml (33 mmol) of methyl chloroformate are added. The mixture is stirred at this temperature for 30 min, then at room temperature for 2 hours. Diluted with 40 ml of water, the mixture is washed with 10 ml of diethyl ether, acidified to pH3 with 3M HCl and extracted with 4×20 ml of ethyl acetate. The pooled organic extracts are washed with water (20 ml), dried over anhydrous sodium sulphate and evaporated at a pressure of 2.0–2.5 kPa. The residue is dissolved in 60 ml of diisopropyl ether and 6 ml (30 mmol) of dicyclohexylamine is added. The separated crystals are filtered off, washed with diisopropyl ether and dried in air.

Yield: 11.5 g (28.5%). $R_f(2)=0.56$. M.p.: 167–170° C. $[\alpha]_D=-37.9°$ (c=0.5, in ethanol). Analysis for $C_{23}H_{36}N_2O_4$ (404.53): Calculated: C%=68.28; H%=8.97; N%=6.92; Found: C%=68.30; H%=9.15; N%=6.75.

Step B: Methoxycarbonyl-3-phenyl-D-alanine 2,4,5-trichlorophenyl ester 11.3 g (28 mmol) of methoxycarbonyl-3-phenyl-D-alanine dicyclohexylammonium salt (Synthesis 2, Step A) is distributed between 75 ml of ethyl acetate and 30.5 ml of 1M $KHSO_4$. The phases are separated, the organic phase is washed neutral with water, dried over anhydrous sodium sulphate and concentrated at a pressure of 2.0–2.5 kPa to a volume of 15 ml. To the cooled (approx. 0° C.) residue 5.5 g (28 mmol) of 2,4,5-trichlorophenol and 5,75 g (28 mmol) of dicyclohexyl carbodiimide are added and the reaction mixture is allowed to stand overnight. The separated dicyclohexylurea is filtered off, and the filtrate evaporated. The oily residue is crystallised from ethanol. The crystals are filtered, washed with diethyl ether and dried in a vacuum desiccator.

Yield: 6.86 g (61%). M.p.: 109–110° C. $R_f(4)=0.84$. Analysis for $C_{17}H_{14}NO_4Cl_3$ (402.66): Calculated: C%=50.70; H%=3.50; N%=3.48; Cl%=26.42 Found: C%=50.80; H%=3.20; N%=3.40; Cl%=26.60.

Step C: Methoxycarbonyl-3-phenyl-D-alanyl-L-proline 4.83 g (12 mmol) of methoxycarbonyl-3-phenyl-D-alanyl-2,4,5-trichlorophenyl ester (Synthesis 2, Step B) is dissolved in 12 ml of pyridine, then 1.38 g (12 mmol) of finely pulverised L-proline and 1.68 ml (12 mmol) of triethyl amine are added with stirring. The reaction mixture is stirred for 16 hours, then evaporated at a pressure of 2.0–2.5 kPa. The residue is dissolved in 40 ml of 5% $NaHCO_3$ and the solution is extracted with 3×7 ml of diethyl ether. The pooled ethereal phases are washed with 7 ml of 5% $NaHCO_3$. The bicarbonate washings are pooled, acidified to pH3 with 3M HCl and extracted with 3×10 ml of ethyl acetate. The extracts are dried over anhydrous sodium sulphate and evaporated at a pressure of 2.0–2.5 kPa. The residue is crystallised with diethyl ether, the crystals are filtered, washed with diethyl ether and dried in a vacuum desiccator.

Yield: 3.05 g (79%). M.p.: 154–157° C. $R_f(2)=0.47$.

The FAB mass spectrum (321 $[M+H]^+$) confirms the assumed structure.

Synthesis 3

Ethoxycarbonyl-3-cyclobutyl-DL-alanyl-L-prolyl-L-arginine aldehyde (Eoc-DL-Cba-Pro-Arg-H) hemisulfate Step 1: Ethoxycarbonyl-3-cyclobutyl-DL-alanyl-L-prolyl-$N^G$-benzyloxycarbonyl-L-arginine lactam Starting with 1.35 g (3.46 mmol) of t-butoxycarbonyl-$N^G$-benzyloxycarbonyl-L-arginine lactam [S. Bajusz et al., J. Med. Chem. 33, 1729 (1990)] and 1.03 g (3.3 mmol) of ethoxycarbonyl-3-cyclobutyl-DL-alanyl-L-proline (Synthesis 3, Step A) the coupling of the components and the chromatographic purification of the end product are performed according to the method described in Example 1, Step 1, using proportional quantities of reagents and solvents. The fractions containing pure end-product [$R_f(1)=0.50$] are pooled, evaporated at a pressure of 2.0–2.5 kPa, the residue is triturated with n-hexane, filtered, washed with n-hexane and dried in a vacuum desiccator.

Yield: 1.0 g (51%). $R_f(1)=0.50$.

ESI mass spectrum (585 $[M+H]^+$) confirms the assumed structure.

Step 2: Ethoxycarbonyl-3-cyclobutyl-DL-alanyl-L-prolyl-$N^G$-benzyloxycarbonyl-L-arginine aldehyde 0.94 g (1.6 mmol) of ethoxycarbonyl-3-cyclobutyl-DL-alanyl-L-prolyl-$N^G$-benzyloxycarbonyl-L-arginine lactam (Synthesis 3, Step 1) is reduced according to the method described in Example 1, Step 2 using proportional quantities of reagents and solvents.

Yield: 0.64 g (68%). $R_f(6)=0.30$.

ESI mass spectrum (587 $[M+H]^+$) confirms the assumed structure.

Step 3: Ethoxycarbonyl-3-cyclobutyl-DL-alanyl-L-prolyl-L-arginine aldehyde hemisulfate 0.59 g (1.0 mmol) of ethoxycarbonyl-3-cyclobutyl-DL-alanyl-L-prolyl-$N^G$-benzyloxycarbonyl-L-arginine aldehyde (Synthesis 3, Step 2) is treated according to the method described in Example 1, Step 3 using proportional quantities of reagents and solvents.

Yield: 0.39 g (78%). HPLC(I): k'=5.55; 6.27 and 7.09.

The FAB mass spectrum (453 $[M+H]^+$, 606 $[M+H+NBA]^+$) confirms the assumed structure.

The starting material can be prepared as follows:

Ethoxycarbonyl-3-cyclobutyl-DL-alanyl-L-proline
(Eoc-DL-Cba-Pro)

Step A: Ethoxycarbonyl-3-cyclobutyl-DL-alanyl-L-proline 1.13 g (5.25 mmol) of ethoxycarbonyl-3-cyclobutyl-DL-alanine (Example 1, Step A) is treated according to the method described in Example 1, Step E using proportional quantities of reagents and solvents to yield the oily 2,4,5-trichlorophenyl ester which is then coupled with 0.58 g (5.0 mmol) of finely pulverised L-proline.

Yield: 1.1 g (71%) of an oil. $R_f(6)=0.53$.

ESI mass spectrum (313 $[M+H]^+$) confirms the assumed structure.

Synthesis 4

Ethoxycarbonyl-3-cyclopentyl-DL-alanyl-L-prolyl-L-arginine aldehyde (Eoc-DL-Cpa-Pro-Arg-H) hemisulfate Step 1: Ethoxycarbonyl-3-cyclopentyl-DL-alanyl-L-prolyl-$N^G$-benzyloxycarbonyl-L-arginine lactam Starting with 3.7 g (9.5 mmol) of t-butoxycarbonyl-N$^G$-benzyloxycarbonyl-L-arginine lactam [S. Bajusz et al. J. Med. Chem. 33, 1729 (1990)] and 2.94 g (9.0 mmol) of ethoxycarbonyl-3-cyclopentyl-DL-alanyl-L-proline (Synthesis 4, Step A), the compounds are treated according to the method described in Example 1, Step 1 using proportional quantities of reagents and solvents. The fractions containing pure end product are pooled, evaporated at a pressure of 2.0–2.5 kPa and the residue is triturated with n-hexane. The solid product is filtered, washed with n-hexane and dried in a vacuum desiccator.

Yield: 2.87 g (54%). $R_f(1)=0.55$.

ESI mass spectrum (599 [M+H]$^+$) confirms the assumed structure.

Step 2: Ethoxycarbonyl-3-cyclopentyl-DL-alanyl-L-prolyl-N$^G$-benzyloxycarbonyl-L-arginine aldehyde 2.75 g (4.6 mmol) of ethoxycarbonyl-3-cyclopentyl-DL-alanyl-L-prolyl-N$^G$-benzyloxyarbonyl-L-arginine lactam (Synthesis 4, Step 1) is reduced according to the method described in Example 1, Step 2 using proportional quantities of reagents and solvents.

Yield: 1.74 g (64%). $R_f(6)=0.42$.

ESI mass spectrum (601 [M+H]$^+$) confirms the assumed structure.

Step 3: Ethoxycarbonyl-3-cyclopentyl-DL-alanyl-L-prolyl-L-arginine aldehyde hemisulfate 1.2 g (2.0 mmol) of ethoxycarbonyl-3-cyclopentyl-DL-alanyl-L-prolyl-N$^G$-benzyloxycarbonyl-L-arginine aldehyde (Synthesis 4, Step 2) is treated according to the method described in Example 1, Step 3, using proportional quantities of reagents and solvents.

Yield: 0.8 g (78%). HPLC(I): k'=3.96; 4.4 and 4.92.

The FAB mass spectrum (467 [M+H]$^+$, 620 [M+H+NBA]$^+$) confirms the assumed structure.

The starting material can be prepared as follows:

Ethoxycarbonyl-3-cyclopentyl-DL-alanyl-L-proline (Eoc-DL-Cpa-Pro)

Step A: Ethoxycarbonyl-3-cyclopentyl-DL-alanyl-L-proline 3.1 g (13,5 mmol) of ethoxycarbonyl-3-cyclopentyl-DL-alanine (Example 4, Step A) is treated according to the method described in Example 1, Step E using proportional quantities of reagents and solvents to yield the oily 2,4,5-trichlorophenyl ester which is then coupled with L-proline.

Yield: 3.1 g (74%). $R_f(6)=0.50$.

ESI mass spectrum (327 [M+H]$^+$) confirms the assumed structure.

Synthesis 5

Ethoxycarbonyl-DL-cyclobutyl-glycyl-L-prolyl-L-arginine aldehyde (Eoc-DL-Cbg-Pro-Arg-H) hemisulfate Starting with 1.2 g (3.0 mmol) of t-butoxycarbonyl-N$^G$-benzyloxycarbonyl-L-arginine lactam [S. Bajusz et al, J. Med. Chem. 33, 1729 (1990)] and 0.69 g (2.3 mmol) of ethoxycarbonyl-DL-cyclobutyl-glycyl-L-proline (Synthesis 5, Step A), the coupling to the respective blocked tripeptide lactam [$R_f(1)=0.32$], the reduction to the blocked tripeptide aldehyde [$R_f(9)=0.53$] and the deblocking are performed according to the method described in Example 1, Steps 1, 2 and 3, using proportional quantities of reagents and solvents.

Yield: 0.22 g.

HPLC(I): k'=2.74; 2.96 and 3.41.

The FAB mass spectrum (439 [M+H]$^+$, 592 [M+H+NBA]$^+$) confirms the assumed structure.

The starting material can be prepared as follows:

Ethoxycarbonyl-DL-cyclobutyl-glycyl-L-proline (Eoc-DL-Cbg-Pro)

Step A: Ethoxycarbonyl-DL-cyclobutyl-glycyl-L-proline 0.78 g (6.0 mmol) of DL-cyclobutyl-glycine [T. H. Porter et al., Arch. Biochem. Biophys, 179, 266 (1977)] is acylated [$R_f(7)=0.60$], made to react with 2,4,5-trichlorophenol [$R_f(4)=0.84$] then coupled with L-proline according to the method described in Example 1, Steps A and E, using proportional quantities of reagents and solvents.

Yield: 03.68 g (50%) of an oil. $R_f(2)=0.17$ and 0.22.

The FAB mass spectrum (299 [M+H]$^+$) confirms the assumed structure.

METHODS

Method M1

Preparation of Clots from Human Plasma a) Platelet-rich plasma is prepared by centrifuging a 9:1 mixture of human blood and 3.8% sodium citrate solution for 5 min. at 240×g.

b) 200 µl platelet-rich plasma and 80 µl 40 mM $CaCl_2$ solution are allowed to stand at room temperature for 1 hour. The thus-formed clot is washed with 6×2 ml of 0.9% NaCl solution with gentle stirring to remove the residual enzymes (thrombin and factor $X_a$). The washing medium is assayed for thrombin-like activity as follows:

c) To 400 µl of washing medium 100 µl of 1 mM Tos-Gly-Pro-Arg-pNA substrate solution is added, the mixture is incubated for 30 min at 37° C., then the reaction is stopped with 100 µl of 50% acetic acid. From this mixture 150 µl aliquots are applied onto a 96-well microtitre plate and the extinction coefficients are measured at 405 nm (ELISA READER SLT Laborinstrument GmbH, Austria). In case of efficient washing the extinction coefficient is smaller than 5% of that of the control.

Method M2

Determination of the Inhibition of Clot-bound Factor Xa a) 0.1–1.0–10 and 100 µg/ml solutions are prepared from the peptide inhibitor in 0.1M Tris-buffer containing 0.02% human albumin (pH=8.5).

b) After draining off the washing medium (Method M1), 400 µl of peptide solution (3 parallel samples for every concentration) is added to the clot and incubated together with 400 µl of buffer as a control for 5 min. at 37° C. Then 100 µl of 2 mM Moc-D-Chg-Gly-Arg-pNA substrate solution is added to each vessel and incubated for another 30 min at 37° C. The reaction is stopped with 100 µl of 50% AcOH.

c) From each reaction vessel 150 µl is applied onto a 96 well microtitre plate and extinction coefficients are measured at 405 nm (ELISA READER SLT Laborinstrument GmbH, Austria). $IC_{50}$ (peptide concentration needed for 50% inhibition) is determined graphically from the average extinctions compared to the control.

Method M3

Determination of the Inhibition of Clot-bound Thrombin a) Solutions are made from the peptide inhibitors according to Method M2/a.

b) After draining off the washing medium the clots (Method M1) are mixed with 400 µl of peptide solution (3 parallel samples with each concentration), then the samples are incubated for 5 min. at 37° C. together with a separate 400 µl buffer serving as control. Then 100 µl Pro-Arg-pNA of 1 mM Tos-Gly-Pro-Arg-pNA substrate solution is added and the incubation continued for further 30 min. at 37° C. The experiment is continued according to M2/c.

Method M4

Preparation of Fibrin Clots a) To each reaction vessel 200 µl of human fibrinogen (SIGMA), 25 µl of 25 NIH/E/ml human thrombin (SIGMA) and 40 µl of 100 mM CaCl$_2$ solution is placed and the mixtures are allowed to stand for 1 hour at 20–22° C. The fibrin clots are washed with isotonic NaCl-solution (3×2 ml) under gentle stirring to remove traces of thrombin and sedimented for 5 min. The effectiveness of the washing can be checked by the method M1/c.

Method M5

Determination of Inhibition of Fibrin-clot Bound Thrombin a) 0.1–1.0–10 and 100 µg/ml solutions are made from the peptide inhibitors with Hepes/NaCl buffer (0.001 M Hepes and 0.1 M NaCl, pH=7.4).

b) Measurements are continued according to M3/b.

Method M6

Determination of Factor Xa Inhibition in Solution on a 96-well Microtitre Plate a) By means of phosphate buffer (0.1M sodium phosphate and 0.05M sodium chloride, pH=7.4) 1.3 E/ml solution is prepared from human factor Xa (SIGMA), and 0.1–1.0–10 and 100 µg/ml solutions from the peptide inhibitors. The Bz-Ile-Glu-Gly-Arg-pNA substrate is used in distilled water solution (0.33 nM).

b) From the control and the peptide inhibitor solutions (3 parallel samples of each concentration) 30–30 µl aliquots are placed into the wells. 30 µl of factor Xa, 90 µl of buffer and 150 µl of substrate are added to the peptide solution and the extinction is determined after 10 min. at 405 nm. Thereafter the steps are the same as in M2/c.

What we claim is:

1. A peptidyl-arginine aldehyde of the formula (I),

Q-D-Xaa-Pro-Arg-H    (I)

wherein

Q represents an acyl group of formula Q'—OCO, wherein Q' represents an alkyl-group with 1–3 carbon atoms, D-Xaa represents a 3-cyclobutyl-D-alanyl- or 3-cyclopentyl-D-alanyl group, Pro represents an L-prolyl group, and Arg represents an L-arginyl group, or an acid-addition salt thereof with an organic or inorganic acid.

2. Ethoxycarbonyl-3-cyclobutyl-D-alanyl-L-prolyl-L-arginine aldehyde or an acid-addition salt thereof.

3. Methoxycarbonyl-3-cyclobutyl-D-alanyl-L-prolyl-L-arginine aldehyde or an acid-addition salt thereof.

4. Ethoxycarbonyl-3-cyclopentyl-D-alanyl-L-prolyl-L-arginine aldehyde or an acid-addition salt thereof.

5. Methoxycarbonyl-3-cyclopentyl-D-alanyl-L-prolyl-L-arginine aldehyde or an acid-addition salt thereof.

6. A pharmaceutical composition which comprises as active ingredient at least one compound of formula (I) defined in claim 1, or a pharmaceutically acceptable acid-addition salt thereof in admixture with pharmaceutically acceptable carriers or additives.

7. The pharmaceutical composition defined in claim 6, wherein the aldehyde of formula (I) is selected from the group consisting of ethoxycarbonyl-3-cyclobutyl-D-alanyl-L-prolyl-L-arginine aldehyde, methoxycarbonyl-3-cyclobutyl-D-alanyl-L-prolyl-L-arginine aldehyde, ethoxycarbonyl-3-cyclopentyl-D-alanyl-L-prolyl-L-arginine aldehyde, methoxycarbonyl-3-cyclopentyl-D-alanyl-L-prolyl-L-arginine aldehyde and acid-addition salts of the foregoing.

* * * * *